United States Patent [19]

Chandraratna

[11] Patent Number: 5,475,113
[45] Date of Patent: Dec. 12, 1995

[54] TETRAHYDRONAPHTHYL AND THIAZOLE, OXAZOLE OR IMIDAZOLE SUBSTITUTED ETHENE DERIVATIVES HAVING RETINOID-LIKE ACTIVITY, REDUCED SKIN TOXICITY AND REDUCED TERATOGENECITY

[75] Inventor: Roshantha A. Chandraratna, Mission Viejo, Calif.

[73] Assignee: Allergan, Inc., Irvine, Calif.

[21] Appl. No.: 260,181

[22] Filed: Jun. 15, 1994

Related U.S. Application Data

[63] Continuation-in-part of Ser. No. 898,764, Jun. 11, 1992, Pat. No. 5,324,840.

[51] Int. Cl.$^6$ ............... C07D 233/76; C07D 263/44; C07D 277/34

[52] U.S. Cl. ............... 548/203; 548/200; 548/204; 548/205; 548/214; 548/235; 548/236; 548/334.5; 548/333.5

[58] Field of Search ............... 548/214, 200, 548/203, 204, 205, 247, 248, 235, 236, 341, 343, 378

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |
| 4,826,969 | 5/1989 | Maignan et al. | 536/55.2 |
| 4,826,984 | 5/1989 | Berlin et al. | 546/134 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |
| 5,324,744 | 6/1994 | Chandraratna | 514/456 |
| 5,324,840 | 6/1994 | Chandraratna | 546/318 |
| 5,326,898 | 7/1994 | Chandraratna | 560/17 |
| 5,344,959 | 9/1994 | Chandraratna | 560/100 |

FOREIGN PATENT DOCUMENTS

| | | |
|---|---|---|
| 0098591 | 1/1984 | European Pat. Off. . |
| 170105A | 6/1986 | European Pat. Off. . |
| 0272921 | 6/1988 | European Pat. Off. . |
| 0303915 | 2/1989 | European Pat. Off. . |
| 3434947 | 4/1986 | Germany . |
| WO9206948 | 10/1991 | WIPO . |

OTHER PUBLICATIONS

Davies et al., *J. Organomettalic Chem* 387 (1990) 381–390.
Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatolgy*, vol. 96, No. 5, May 1991, pp. 792–797.
Organ maintenance of human sebaceous glands: in vitro effects of 13–cis retinoic acid and testosterone, John Ridden, et al., *Journal of Cell Science*, vol. 95, 1990, pp. 125–136.
Characterization of Human Sebaceous Cells In Vitro, Thomas I. Doran, et al., *The Journal of Investigative Dermatology*, vol. 96, No. 3, Mar. 1991, pp. 341–348.
Synthesis and Evaluation of Stilbene and Dihydrostilbene Derivatives as Potential Anticancer Agents That Inhibit Tubulin Polymerization by Cushman, Mark et al., *J. Med. Chem.* 1991, 34, 2579–2588.
Synthesis and Evaluation of New Protein–Tyrosine Kinase Inhibitors. Part 1. Pyridine–Containing Stilbenes and Amides by Cushman, Mark et al., *Bioorganic & Medicinal Chemistry Letters*, vol. 1, No. 4, pp. 211–214, 1991.
Di–and Tri–methoxystyryl Derivatives of Heterocyclic Nitrogen Compounds by Bahner, C. T. et al., *Arzneim—Forsch./Drug Res*, 31 (I), Nr. 3 (1981).
Retinobenzoic acids. 3. Structure–Activity Relationships of retinoidal Azobenzene–4–carboxylic acids and Stilbene–4–carboxylic acids by H. Kagechika et al., *Journal of Medicinal Chemistry*, 1989, 32, pp. 1098–1108.

*Primary Examiner*—Raymond Henley, III
*Assistant Examiner*—Phyllis G. Spivack
*Attorney, Agent, or Firm*—Gabor L. Szekeres; Robert J. Baran; Martin A. Voet

[57] ABSTRACT

Compounds of the formula

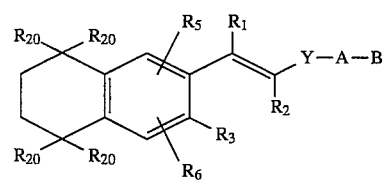

as herein defined, have retinoid-like activity and are substantially non-teratogenic and non-irritating to the skin.

32 Claims, No Drawings

TETRAHYDRONAPHTHYL AND THIAZOLE, OXAZOLE OR IMIDAZOLE SUBSTITUTED ETHENE DERIVATIVES HAVING RETINOID-LIKE ACTIVITY, REDUCED SKIN TOXICITY AND REDUCED TERATOGENECITY

CROSS-REFERENCE TO RELATED APPLICATION

The present application is a continuation-in-part of application Ser. No. 07/898,764 filed on Jun. 11, 1992, issued as U.S. Pat. No. 5,324,840.

FIELD OF THE INVENTION

The present invention is directed to novel compounds which have retinoid like activity and which lack substantial teratogenic activity and have substantially reduced skin toxicity. The present invention is also directed to pharmaceutical compositions adapted for administering the novel compounds to mammals including humans.

BRIEF DESCRIPTION OF THE PRIOR ART

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

The compounds developed in the prior art with retinoid like properties, are, however, not without disadvantages. Several such prior art compounds cause serious irritation when applied to the skin (which is an important mode of application for treatment of skin conditions) and cause skin toxicity when administered orally as well. Many of the prior art compounds having retinoid like activity are teratogenic. Teratogenecity or teratogenic activity can be defined as an undesirable effect of a drug on a developing fetus. It is generally accepted in the art that pregnant females, and even females who are not pregnant but in the child-bearing age should avoid teratogenic drugs.

In light of the foregoing, there is a significant need in the prior art for pharmaceutical compositions, methods of treatment and new chemical entitities which are effective as treatment of the diseases and conditions for which retinoid like compounds are usually applied, and which have reduced or no teratogenic activity and cause no significant irritation on the skin.

With respect to specific compounds or classes of compounds having retinoid like or other biological activity, the following examples are noted.

Great Britain Patent GB 2190-378 describes tetramethyl-tetrahydronaphthylpropenylphenol compounds, examples of which are ortho, meta or para (E)-2-(5,6,7,8-tetrahydro-5,5,8,8-tetramethyl-2-naphthyl)propenyl)phenol.

German Patent DE 3602-473 A discloses aralkenylphenol derivatives, examples of which are (E)-1-(4-hydroxyphenyl)-2-(5,6,7,8-tetrahydro-5,5,8,8-tetramethyl-2-naphthyl-)propene and (E)-1-(4-methoxyphenyl)-2-(5,6,7,8-tetrahydro-5,5,8,8-tetramethyl- 2-naphthyl)propene.

European Patent EP 176 033 A discloses isoxazolylvinyl indane and tetrahydronaphthalene derivatives, an example of which is (E)-5-[2-(3-fluoro-5,5,8,8-tetramethyl- 5,6,7,8-tetrahydro-2-naphthyl)-1-propenyl]-isoxazole-3-carboxylic acid.

The publication EP 303 915 discloses indanyl and tetrahydronaphthyl and substituted phenyl propenes as retinoids, where the phenyl substituent is sulfur substitited. An example of the disclosed compounds is methyl 4-(2-(5,6,7, 8-tetrahydro-5,5,8,8-tetramethyl-2-naphthyl(propenyl)phenylsulphone.

European patent EP 176 032 A discloses 6-styryltetrahydronaphthalene derivatives, examples of which are (E)-4-[2-(5,6,7,8-tetrahydro-5,5,8,8-tetramethyl-7-hydroxy-2-naphthalenyl)-1-propenyl]benzylalcohol, and (E)-4-[2-(5,8-dihydro-5,5,8,8-tetramethyl-2-naphthalenyl)- 1-propenyl] benzoic acid.

U.S. Pat. No. 4,326,055 discloses ethene derivatives which have a substituted phenyl ring and a substituted indane or tetrahydronaphtalene group. The compounds are described as tumor inhibiting agents, and useful for treating dermatological conditions and rheumatic illnesses.

U.S. Pat. No. 4,740,519 discloses certain aromatic heterocycle derivatives which have retinoid like activity.

Published European Patent Application 0 253 302 discloses propene derivatives substituted with a tetrahydronaphthyl group and a heterocycle, where the heterocycle group is said to include oxazole, isooxazole and thiazole.

Several co-pending applications and recently issued patents of the present inventor, which are assigned to the assignee of the present application, are directed to further compounds having retinoid like activity.

SUMMARY OF THE INVENTION

It has been discovered in accordance with the present invention that the partial structure or moiety shown in Formula 1 below, imparts significantly reduced teratogenic activity, and reduces skin toxicity in a class of disubstituted ethene compounds which have retinoid like or related biological activity.

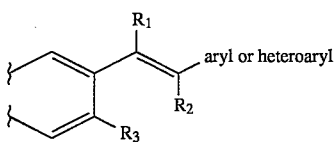

Formula 1

In Formula 1 the partially drawn ring signifies an aromatic ring which may be carbocyclic or heteroaromatic, 6-membered or 5-membered, and may be condensed with another ring as particularly described below. $R_1$ is lower alkyl, Cl, Br, or I, $R_2$ is H, lower alkyl, Cl, Br, or I, and $R_3$ is lower alkyl, Cl, Br, I, or is an ether, thioether, ester, thioester, amine or substituted amine group. It is an important feature of the present invention that the ethene moiety (double bond) is connected to an aromatic ring where the aromatic carbon adjacent to the carbon directly connected to the double bond (in other words the carbon in the ortho position) has a substituent ($R_3$) with some steric bulk (other than hydrogen) and that the carbon of the olefinic double bond which is attached to the ortho substituted aromatic ring is also substituted with a substituent ($R_1$) other than hydrogen.

In light of the foregoing, the present invention covers a method of treating animals of the mammalian species, including humans, and particularly females of child-bearing age and pregnant females, with a substantially non-teratogenic pharmaceutical composition comprising one or more compounds having the partial structure shown in Formula 1 as the active ingredient, for treatment of the diseases or conditions against which retinoid like compounds are useful, namely as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myelorid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus, for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

The present invention is also directed to the pharmaceutical compositions used in the above-noted methods of treatment.

The present invention particularly covers methods for treating diseases and conditions where retinoid like compounds are effective for treatment, but their use is limited because of their generally known skin toxicity.

New chemical compounds of the present invention which are active ingredients in the pharmaceutical compositions of the invention, are characterized by Formula 2,

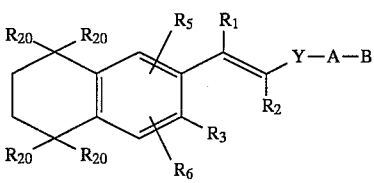

Formula 2 where $R_1$ is lower alkyl, Cl, Br, or I;

$R_2$ is H, lower alkyl, Cl, Br, or I;

$R_3$ is lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}COR_{11}$;

$R_5$ and $R_6$ independently are H, lower alkyl, Cl, Br, I, lower alkoxy or lower thioalkoxy of 1 to 6 carbons;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is H, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2–5 carbons;

$R_{20}$ is independently H or lower alkyl, and

Y is oxazole, thiazole, imidazole, isooxazole, isothiazole or isoimidazole which may be optionally substituted on a carbon or on a nitrogen with an $R_{21}$ group which is lower alkyl, or a dialkylsulfonamido group of the formula $SO_2NR_{22}R_{23}$ wherein $R_{22}$ is lower alkyl, and $R_{23}$ is lower alkyl or H.

GENERAL EMBODIMENTS

Definitions

The term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. Where B (of Formula 2, 3, 4, 5 and 6) is —COOH, this term covers the products derived from treatment of this function with alcohols, preferably with aliphatic alcohols having 1-6 carbons. Where the ester is derived from compounds where B is —$CH_2OH$, this term covers compounds of the formula —$CH_2OOCR_{11}$ where $R_{11}$ is any substituted or unsubstituted aliphatic, aromatic or aliphatic-aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is $(-OR)_2$. Here, R is lower alkyl. Also, K may be $-OR_1O-$ where $R_1$ is lower alkyl of 2–5 carbon atoms, straight chain or branched.

A pharmaceutically acceptable salt may be prepared for any compound of this invention, if the compound has a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention contain at least one double bond and therefore may have trans and cis (E and Z) isomers. In addition, some of the compounds may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

Methods of Administration

The compounds of this invention may be administered systemically or topically, depending on such considerations as the condition to be treated, need for site-specific treatment, quantity of drug to be administered, and similar considerations.

In the treatment of dermatoses particularly, topical administration may be used, though in certain cases such as treatment of severe cystic acne, oral administration may be preferred. Any common topical formulation such as a solution, suspension, gel, ointment, or salve and the like may be used. Preparation of such topical formulations are well described in the art of pharmaceutical formulations as exemplified, for example, by *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoid like compounds will be effected by administration of the therapeutically effective dose of one or more compounds in accordance with the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 10 mg per kg body weight per day, but preferably about 0.1 to 10 mg/kg, will effect a therapeutic result in most instances.

Biological Activity

The compounds have no teratogenic activity, or are substantially less teratogenic than comparable prior art compounds. The lack of or reduced teratogenecity of these compounds can be demonstrated by an in vivo teratology study involving gestating ICR mice. The methodology of the study is described as follows:

Animals

ICR mice (Ace Animals, Boyertown, Pa.) are used. Mature male and virgin female ICR mice are housed in environmentally controlled rooms and acclimatized to a 12 hour light/dark cycle (light cycle 6 A.M. to 6 P.M.) for 2 weeks prior to use. All animals are maintained on Purina Lab Chow and tap water ad libitum. A group of 3–4 females are caged with a single male of proven fertility for 4 hours. Presence of a vaginal plug immediately afterward is regarded as evidence of successful mating, and this day is designated as day 0 of gestation.

Teratology

A single oral dose (0.1, 1.0, 10 or 100 mg/kg) of the test drug is administered on the morning (10 A.M.) of day 11 of gestation. All animals are killed by cervical dislocation under mild ether anesthesia on day 17 of gestation. Upon laparotomy, the fetuses are examined for external malformations and weighed; one-half of each litter is then fixed in 95% ethanol and processed for staining of the skeleton by the rapid, alizarin red-S dye method. These preparations were examined under a dissection microscope to screen for abnormalities in the axial and the appendicular skeleton. The other half of each litter is fixed in Bouin's solution and examined by freehand razor serial sectioning to screen for anomalies of the brain, face, and palate.

Differences in dose-related incidence of malformations and resorptions are assessed by computing percentages of affected conceptuses among total implantation sites. The groups are compared statistically by a method based on Student's t-tests of arcs in square root transformed percentages. Values at 0.05 probability level are considered significant. The median effective dose is calculated by logarithmic curve fitting of the dose-response data.

The lack of or substantially reduced teratogenecity of the compounds of this invention can also be demonstrated in an in vitro bioassay which measures inhibition of chondrogenesis (bone formation) in chick embryo cells as a classic measure of teratogenecity the results. The assay is described as follows:

High-density "spot" cultures of limb bud mesenchymal cells are used to compare the ability of various concentrations of test drugs to suppress chondrogenic differentiation as a bioassay. Forelimb buds of mouse embryos on day 12 of gestation (54±2 somites) are dissociated in a trypsin-EDTA solution, and the resultant single-cell suspension is plated as 20-µl spots (200,000 cells/spot) on plastic culture dishes. Retinoid concentrations ranging from 0.3 ng/ml to 3 µg/ml (1 nM-10 µM) are added to the culture medium (Eagle's MEM+10% fetal bovine serum, GIBCO) 24 hours after initial plating. Control cultures receive only the vehicle (ethanol, concentration ≦1% by vol); Retinoic acid is used as a positive control in another set of cultures.

The cultures are terminated 96 hours after plating, at which time the medium is removed and the cells are fixed for 1 hour in 10% formalin containing 0.5% cetylpyridinium chloride. The cultures are rinsed in acetic acid and stained for 1 hour in 0.5% Alcian blue solution at pH 1.0, differentiated in 3% acetic acid, and then dehydrated in ethanol and scored for chondrogenesis under the microscope. An absence or reduction in the number of cartilage nodules in stained cultures as compared with control cultures is taken as a measure of suppression of chondrogenesis. The number of cartilage nodules stained in the whole spot, mean number of nodules, and standard deviations are calculated for four replicate cultures per treatment. The median concentration causing a 50% inhibition of chondrogenesis compared with controls ($IC_{50}$) is calculated by logarithmic curve fitting of the dose-response data.

A pharmacokinetic study involving the oral intubation of mice with a dose (e.g. 10 mg/kg) of a compound in accordance with the present invention, and subsequent measurement of the concentration of the drug in the maternal plasma and in the embryo, can be used to reveal the concentration of the test compound in the maternal plasma and in the embryo.

The retinoid like activity of the novel compounds of the invention can be confirmed by several assay procedures. An assay involving human sebocyte cultures measures the inhibition of $^3$H-thymidine into cells, and thus measures inhibition of DNA synthesis and thus an anti-proliferative effect on sebocyte (i.e. a sebostatic effect). This assay is also considered a specific assay for effectiveness of a compound as a potential anti-acne drug. The test is conducted as follows.

SOURCE OF SKINS:

Face-lift or forehead reduction skins from cosmetic surgeries are used as sources of human sebaceous gland cells (sebocytes).

ISOLATION OF SEBOCYTES:

Isolated sebocytes are plated in type 1 collagen coated-dishes in DMEM/F12 (1:1) medium supplemented with 8% fetal bovine serum, 2% human serum, 10 ng/ml epidermal growth factor, 1 nM cholera toxin, 1 µM hydrocortisone, and penicillin/streptomycin/amphotericin B. Secondary cultures are prepared by plating Dispase dissociated cells in collagen coated 24-well plates.

PROLIFERATION STUDIES ($^3$H-THYMIDINE INCORPORATION):

Sub-confluent secondary cultures are treated with the test compounds or ethanol vehicle every 2–3 days for 8 days in the above medium from which the total serum concentration is reduced to 2% and hydrocortisone is not included. During the last 6 hours of treatment, the cultures are labeled with 2 µCi/ml $^3$H-thymidine. DNA from the cells is extracted by trichloroacetic acid and perchloric acid, and assayed for radioactivity by scintillation counting and for content of DNA by the diphenylamine colorimetric method. The results are expressed as CPM/µg DNA, or as per cent of vehicle control which incorporated about 1,000–1,500 cpm/µg DNA.

Other assays in which the retinoid like activity of the compounds of the invention can be confirmed are the HL-60 transglutaminase induction and HL-60 differentiation assay, the procedures of which are described as follows.

DIFFERENTIATION: HL-60 CELLS NITROBLUE TETRAZOLIUM REDUCTION ASSAY (NBT REDUCTION ASSAY)

HL-60 cells are grown as a suspension culture in T-162 $CM^2$ flasks in serum-free RPMI 1640 medium supplemented with insulin (5 µg/ml), transferrin (5 µg/ml), and selenium (3 nM). The cells ($1\times10^5$/well in 24-well dishes) are treated with serial dilutions of test compounds in the above RPMI 1640 medium which is additionally supplemented with 0.2 mM dibutyryl cyclic adenosine monophosphate, a component found to be necessary for efficient differentiation of the cells. Ethanol is used in the vehicle control cultures. After 3 days of incubation at 37° C. in a 5% $CO_2$ incubator, nitroblue tetrazolium (NBT) and tetradecanoylphorbol acetate (TAP), at final concentrations of 0.1% and 100 ng/ml, respectively, are mixed with the cells and incubated at room temperature for 15 to 30 minutes. Differentiated HL-60 cells acquire a purple deposit of formazan (NBT positive cells) from the reduction of NBT. The cells are then fixed in 10% paraformaldehyde and pelleted by centrifugation. The cell pellets are resuspended in a small volume of phosphate buffer saline. The number of NBT positive cells and the total number of cells of each cell suspension is determined by counting in a hemacytometer. The mean of quadruplicate cultures is expressed as per cent of NBT positive cells.

As it will be readily understood by those skilled in the art, differentiation of cells in this assay is a marker of useful retinoid like activity.

TISSUE TRANSGLUTAMINASE ASSAY (tTGASE) IN

HL-60 CELLS

HL-60 cells are grown as a suspension culture in T-162 cm² flasks in serum-free RPMI 1640 medium supplemented with insulin (5 µg/ml), transferrin (5 µg/ml), and selenium (3 nM). The cells (1×10⁶ cells/well, in 6-well dishes) are treated with serial dilutions of test compounds in the above RPMI 1640 medium which is additionally supplemented with 1 nM dibutyryl cyclic adenosine monophosphate, a component found to be necessary for efficient differentiation of the cells. Ethanol is used in the vehicle control cultures. After 1 days of incubation at 37° C. in a 7.5% $CO_2$ incubator, the cells are collected in a set of tubes and pelleted by centrifugation. The cells are lyzed in a buffer containing 20 mM Tris-HCl, pH 7.5, 1 mM EDTA, and 0.5% Triton X-100. An aliquot of the cell lysate is assayed for tTGASE activity in a reaction mixture containing 20 mM Tris-HCl, pH 7.5, 5 mM $CaCl_2$, 2 mg/ml dimethylcasein, 15 mM B-mercaptoethanol and 50 µCi/ml [2,3-³H] putrescine dihydrochloride. The reaction is carried out for 60 minutes in a 37° C. shaking water bath. The reaction is stopped by an addition of 10% trichloroacetic acid containing 0.1% putrescein. An aliquot of the stopped reaction mixture is spotted on Whatman 3 MM filter discs. The filter discs, along with the control blank filter discs, are washed twice with 5% trichloroacetic acid containing 0.1% putrescein and twice with methanol. After drying under a heat lamp, the radioactivity in the filter discs is determined by scintillation counting. An aliquot of the cell lysates is also assayed for protection concentration by the Bradford method (Bio-Rad). After subtracting the radioactivity from the control blank filter discs, the data are calculated and expressed as pmol/min/mg protein.

As is well understood in the art, induction of tranglutaminase activity in the just-described assay is an early marker of retinoid like activity.

The retinoic acid-like activity of these compounds can also be confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. Activity of exemplary compounds of the present invention in the above-described ODC assay is disclosed in Table 1 which provides either $IC_{80}$ (or other measured per cent inhibition at the indicated concentration) for the respective exemplary compound. ("$IC_{80}$" is that concentration of the test compound which causes 80% inhibition in the ODC assay; by analogy, e.g. $IC_{50}$ would be that concentration which causes 50% inhibition.)

TABLE 1

| Compound# | $IC_{80}$ conc (nmols) |
| --- | --- |
| 1 | 394 |

TABLE 1-continued

| Compound# | $IC_{80}$ conc (nmols) |
| --- | --- |
| 2 | 1000 |
| 4 | 569 |

Ability of the compounds of the invention to act as ligands in RAR and RXR retinoid receptors can be assayed in accordance with the assay procedure described by Boehm et al. titled "Synthesis of High Specific Activity [³H]-9-cis-Retinoic Acid and Its Application for Identifying Retinoids with Unusual Binding Properties", Journal of Medicinal Chemistry, 1994, 37, 408–414. As it has been relatively recently developed in the art, both the RAR and RXR retinoid receptors have subtypes, which are respectively termed RARα, RARβ, RARΓ, and RXRα, RXRβ, RXRΓ. Whereas activity in any one of the receptor subtypes, or in all of them, is a marker of retinoid-like activity, differentiation between the RAR and RXR receptors, and even differentiation among the subtypes is a desirable pharmacological property. Especially, it is understood that compounds which are specific or selective to RXR receptors, that is compounds which have significantly greater binding affinity to the RXR receptors than to the RAR receptors, tend to have significantly reduced skin toxicity and reduced teratogenecity. Activity of a test compound in the above-referenced assay is expressed in $EC_{50}$ in nanomoles, the smaller the $EC_{50}$ concentration, the greater the affinity of the test compound to the respective receptor subtype. Table 2 below shows the activity of exemplary Compound 1 of this invention in the referenced retinoid receptor assay.

TABLE 2

| $EC_{50}$ of Compound 1 | | | | | |
| --- | --- | --- | --- | --- | --- |
| RARα | RARβ | RARΓ | RXRα | RXRβ | RXRΓ |
| NA¹ | 220 | 200 | 4.4 | 2.8 | 3.8 |

¹NA = not active

Another advantageous property of the compounds of the present invention is that the compounds show significantly less toxicity and cause significantly less skin irritation than comparable compounds lacking the structural features in accordance with the present invention. The lessened toxicity of the compounds is significant, because toxicity, and specifically irritation of skin is considered a general disadvantage of retinoid like compounds. Therefore, the fact that the structure shown in Formula 1 imparts significantly lessened toxicity and skin irritating effect to the compounds in accordance with the present invention, is surprising and remarkable.

Specifically, a test to determine skin toxicity of a test compound is termed "Two Week Acute Skin Toxicity Study after Multiple Topical Applications in Female Hairless Mice" and is conducted as follows. A daily dose (expressed in nanomoles) of the "test compound" is applied to the skin on the back of hairless mice (usually a test group of 5 mice for a given compound). The daily dose of the test compound is applied for 5 consecutive days, followed by two days when the test compound is not administered, and is thereafter administered again for 4 more consecutive days. On the 14th day the test animals, if still alive, are sacrificed to perform certain studies and tests. In the meanwhile certain tests and observations are made on a daily basis with respect to body weight and skin condition. Skin condition is graded as "flaking/scaling" and "abrasion" on a scale of 0 to + 5 where the various numbers correspond to the following observations.

| Primary Skin Irritation Scoring Scale | Grade |
|---|---|
| Flaking/scaling | |
| No flaking | 0 |
| Very slight (few flakes) | +1 |
| Slight (~25% or less) | +2 |
| Mild (greater than ~25%, less than ~50%) | +3 |
| Moderate (greater than ~50%, less than ~75%) | +4 |
| Severe (~75% or more) | +5 |
| Abrasion | |
| No abrasion | 0 |
| Very slight (One to two abrasions with a slight pink color) | +1 |
| Slight (One or more abrasions, dark pink color) | +2 |
| Mild (greater than ~25%, light red color) | +3 |
| Moderate (greater than ~50%, red color) | +4 |
| Severe (greater than ~75%, deep red color) | +5 |

Preferred Embodiments

Referring now to Formulas 2 and with reference to the symbol A depicting in effect a side chain on the heterocyclic group (represented by Y), compounds are preferred in accordance with the invention, where A is $(CH_2)_n$. Still more preferred are compounds where n is zero.

With respect to the symbol B in Formula 2, compounds are preferred in accordance with the invention where B is —COOH, or an alkali metal salt or organic amine salt thereof. Alternatively, compounds are preferred where B is represented by $COOR_8$ (ester where $R_8$ is lower alkyl), $CONR_9R_{10}$ (amide) —$CH_2OH$ (alcohol), $CH_2OCOR_{11}$, $CH_2OR_{11}$ ($R_{11}$ is lower alkyl; lower alkyl esters and ethers formed with a lower alkanol).

With respect to the symbol Y in Formula 2, compounds are preferred in accordance with the present invention where Y is thiazole or imidazole. Preferably the thiazole group is attached to the substituted ethenyl group at the 2 position of the ring, and the A-B B group is preferably attached to the thiazole at the 5 position of the ring. When the Y group is imidazole, the substituted ethenyl group is preferably attached to the 4-position of the ring, and the A-B substituent is preferably attached at the 2 position of the ring. Alternatively the substituted ethenyl group is preferably attached to the 2-position of the imidazole ring, and the A-B substituent is preferably attached at the 5 position of the imidazole ring.

With respect to the symbol $R_2$ in Formula 2, $R_2$ is preferably hydrogen or lower alkyl, more preferably hydrogen.

The substituent $R_1$ is preferably lower alkyl, and most preferably methyl. $R_3$ is preferably lower alkyl or halogen, and most preferably methyl, chloro or bromo.

The $R_5$ and $R_6$ substituents are preferably hydrogen or lower alkyl, more preferably hydrogen.

The symbols $R_{20}$ preferably represent lower alkyl groups, and most preferably methyl groups. With respect to the optional $R_{21}$ substituent on the Y ring preferably it is methyl or $SO_2NR_{22}R_{23}$ where $R_{22}$ and $R_{23}$ preferably are methyl.

The most preferred compounds of the present invention are shown below in Table 3 with reference to Formula 3 and Formula 4. In Table 3 the substitution pattern of the imidazole ring is indicated, the first number refers to attachment of the ethenyl group, and the second number to the attachment of the $COOR_8$ group to the imidazole ring, the numbering of which is shown in Formula 4.

TABLE 3

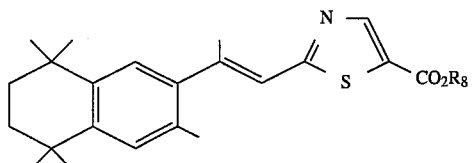

Formula 3

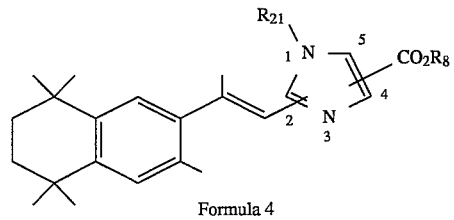

Formula 4

| Compound # | Formula | $R_{21}$ | $R_8$ | subst. |
|---|---|---|---|---|
| 1 | 3 | — | H | — |
| 2 | 4 | $CH_3$ | $C_2H_5$ | 4,2 |
| 3 | 4 | H | $C_2H_5$ | 4,2 |
| 4 | 4 | $SO_2N(CH_3)_2$ | $C_2H_5$ | 4,2 |
| 5 | 4 | H | $C_2H_5$ | 2,5 |
| 6 | 4 | H | H | 2,5 |
| 7 | 4 | $CH_3$ | $C_2H_5$ | 2,5 |
| 8 | 4 | $SO_2N(CH_3)_2$ | $C_2H_5$ | 2,5 |
| 9 | 4 | $SO_2N(CH_3)_2$ | H | 2,5 |

Synthetic Procedures for Obtaining the Compounds in Accordance with the Invention The novel compounds of the invention can be made by a number of different synthetic chemical pathways. To illustrate the invention the following synthetic schemes are provided. The synthetic chemist will readily appreciate that the conditions set out here are specific embodiments for making novel compounds of the invention which can be generalized to any and all novel compounds described in the present specification.

REACTION SCHEME 1

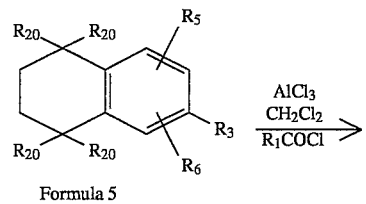

Formula 5

-continued
REACTION SCHEME 1

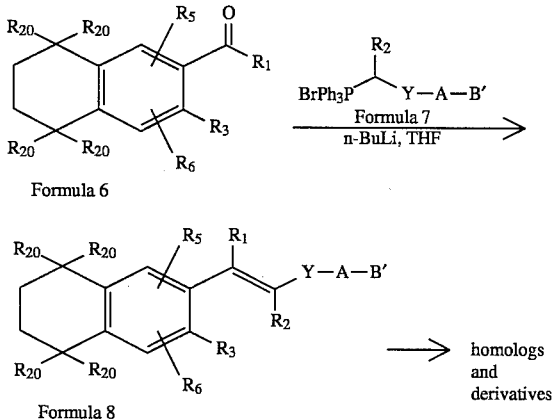

Formula 6

Formula 8

⟶ homologs and derivatives

Referring to Reaction Scheme 1, a 5,5,7,8tetrahydronaphthyl compound (Formula 5) which has the desired $R_3$, $R_5$, $R_6$ and $R_{20}$ substituents (as these are defined in connection with Formula 2) is reacted under Friedel Crafts-like conditions with a reagent such as $R_1COCl$ ($R_1$ is defined as in connection with Formula 2) to introduce the $R_1$—CO— ketone function into the 2-position of the tetrahydronaphthalene nucleus. When $R_1$ is methyl, then the reagent in the Friedel Crafts type reaction is typically acetyl chloride. The resulting ketone of Formula 6 is then subjected to a Wittig reaction with a triphenylphosphonium halide (Wittig) reagent of Formula 7. The Wittig reagent of Formula 7 carries the A-B' functionality, where B' is either the group B as defined in connection with Formula 2, or is a suitably blocked or protected derivative thereof. The Wittig reaction is conducted in the presence of strong base, such as n-butyllithium in a solvent like tetrahydrofuran (THF), as is indicated in the reaction scheme. The ethylenic bond (double bond) of the compounds of Formula 8 is formed in this reaction. As is stated above, when B' is B then the compounds of Formula 8 are the same as compounds of Formula 2, otherwise compounds of Formula 8 are protected or blocked derivatives of the compounds of Formula 2.

The compounds of Formula 8 may be subjected to further transformations, particularly as far as synthetic transformation of the A-B' group is concerned. Regarding these transformations the following well known and published general principles and synthetic methodology are noted.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before affecting the Wittig or a Horner Emmons (or analogous) coupling reaction of Reaction Scheme 1 (where such compounds corresponding to Formula 7 are not available from a commercial source) aromatic or heteroaromatic carboxylic acids are subjected to homologation by successive treatment under Arndt-Eistert conditions or other homologation procedures. Alternatively, derivatives which are not carboxylic acids may also be homologated by appropriate procedures. The homologated acids can then be esterified by the general procedure outlined in the preceding paragraph.

An alternative means for making compounds where A is $(CH_2)_n$ (n is 1–5) is to subject the compounds of Formula 2, (or of Formula 8) where B is an acid or other function, to homologation, using the Arndt-Eistert method referred to above, or other homologation procedures.

Compounds of Formula 2, or of Formula 8 where A is an alkenyl group having one or more double bonds can be made for example, by having the requisite number of double bonds incorporated into the intermediate which is coupled as a triphenylphosphonium halide (Wittig reagent) or as phosphonate (Horner Emmons reagent) with the ketone of Formula 6. Generally speaking, such compounds where A is an unsaturated carbon chain can be obtained by synthetic schemes well known to the practicing organic chemist; for example by Wittig, Horner Emmons and like reactions, or by introduction of a double bond by elimination of halogen from an alpha-halo-alkyl-carboxylic acid, ester or like carboxaldehyde. Compounds of Formula 2 or of Formula 8 where the A group has a triple (acetylenic) bond can be made by using the corresponding phosphonate intermediate. Such intermediate can be obtained by reactions well known in the art, for example, by reaction of a corresponding aromatic methyl ketone with strong base, such as lithium diisopropyl amide.

The acids and salts derived from compounds of Formula 2 and of Formula 8 are readily obtainable from the corresponding esters. Basic saponification with an alkali metal base will provide the acid. For example, an ester of Formula 2 or of Formula 8 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.,* 399, 1979), or dimethyl sulfoxide/oxalyl chloride in methylene chloride (Omura, K., Swern, D., *Tetrahedron,* 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

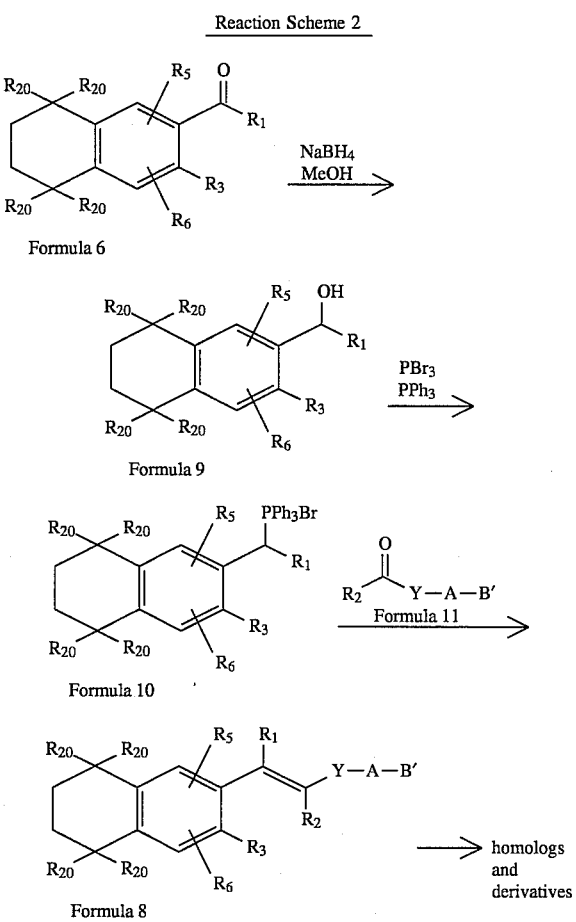

Reaction Scheme 2

Reaction Scheme 2 illustrates another example of a synthetic procedure for preparing the compounds of the invention.

Thus, in accordance with this reaction scheme, the ketone of Formula 6 is reduced (for example with sodium borohydride) to the corresponding alcohol of Formula 9. The alcohol of Formula 9 is converted to the corresponding phosphonium salt (for example triphenyl phosphonium bromide) by treatment with the appropriate reagents, such as phosphorous tribromide and triphenylphosphine. The phosphonium salt of Formula 10 is a Wittig reagent, which is reacted with a heteroaryl aldehyde of Formula 11, under Wittig conditions (base such as n-butyl lithium). In Formula 11 the B' group is either the same as the B group defined in connection with Formula 2, or a suitably blocked or protected derivative thereof. The compound of Formula 8 is the result of the latter reaction which when necessary can be converted into compounds of Formula 2 by deblocking or deprotection, and/or by further transformations as noted above. This is indicated in the reaction scheme by reference to conversion into homologs and derivatives.

Examples of reagents in accordance with Formulas 6 and 7 to be used in the Horner Emmons or Wittig and analogous coupling reactions to provide the compounds of the present invention, are as follows:

Methyl (5,6,7,8-tetrahydro-3,5,5,8,8-pentamethyl-naphthalen- 2-yl) ketone;

1-[(5,6,7,8-tetrahydro-3,5,8,8-pentamethyl-naphthalen-2-yl)ethan-1-yl]triphenylphosphonium bromide;

Methyl (3-chloro-5,6,7,8-tetrahydro-5,5,8,8-tetramethyl-naphthalen- 2-yl) ketone;

[(3-chloro-5,6,7,8-tetrahydro-5,5,8,8-tetramethyl-naphthalen- 2-yl)ethan-1-yl]triphenylphosphonium bromide;

Methyl (3-bromo-5,6,7,8-tetrahydro-5,5,8,8-tetramethyl-naphthalen- 2-yl) ketone;

Methyl (3-ethyl-5,6,7,8-tetrahydro-5,5,8,8-tetramethyl-naphthalen- 2-yl) ketone, and Methyl (5,6,7,8-tetrahydro-5,5,8,8-tetramethyl-3-isopropylnaphthalen- 2-yl) ketone.

An alternative and presently preferred method for synthesizing the compounds of the present invention is shown in Reaction Scheme 3.

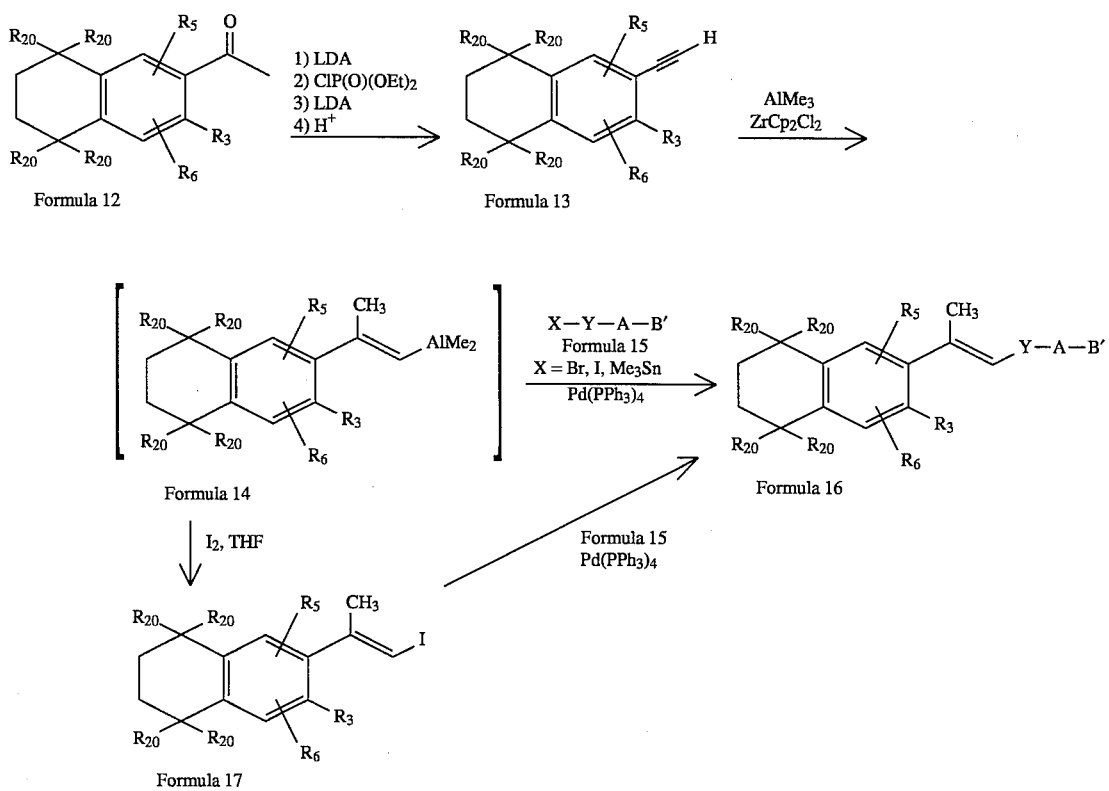

Reaction Scheme 3

In accordance with this scheme, the methyl ketone of Formula 12 is used as a starting material. This methyl ketone can be obtained in accordance with Reaction Scheme 1 from the tetrahydronaphthalene compound of Formula 5 by Friedel Crafts reaction with acetyl chloride. The methyl ketone of Formula 12 is converted into the 2-ethynyltetrahydronaphthalene derivative of Formula 13. This is accomplished, preferably by treatment with lithium diisopropylamide (at low temperature, such as −78 degrees C.) which causes enolization of the acetyl group. The intermediate enol compound (not shown in Reaction Scheme 3) is phosphorylated by treatment with diethylchlorophosphate (or the like) and is again reacted at reduced temperature (e.g. −78 degrees C.) with lithium diisopropylamide, to form the triple bond (presumably by an elimination reaction) and to yield the 2-ethynyltetrahydronaphthalene derivative (Formula 13).

It is noted at this point that the present invention is not intended to be limited or bound by the above-mentioned and other theories of reaction mechanisms. Brief description of theory of reaction mechanisms (where applicable) are given to further enable and facilitate the work of a skilled artisan in the field to modify and adjust the synthetic conditions to fit particular specific intermediates and to make the several compounds of the invention, without departing from the scope and spirit of the invention.

An alternative synthetic route (not shown in Reaction Scheme 3) to introduce the acetylene (ethyne) portion into the molecule so as to obtain the 2-ethynyltetrahydronaphthalene derivative of Formula 13 is to react a 2-bromotetrahydronaphthalene derivative (such as a 2-bromo compound derived from Formula 5) with trimethylsilylacetylene in the presence of cuprous iodide and a suitable catalyst, typically having the formula $Pd(PPh_3)_2Cl_2$. The reaction is typically conducted in the presence of the just-noted catalyst, an acid acceptor, (such as triethylamine) under an inert gas (argon) atmosphere, by heating in a sealed tube. The trimethylsilyl moiety can be removed from the resulting 2(trimethylsilyl)ethynyltetrahydronaphthalene under basic conditions, preferably in an inert gas atmosphere. An analogous reaction sequence which introduces the ethyne moiety into the 6-position of a thiochroman nucleus is described in U.S. Pat. No. 5,183,827, the specification of which is incorporated herein by reference.

Referring back to Reaction Scheme 3, the ethyne compound of Formula 13 is reacted with trimethylaluminum $((CH_3)_3Al)$ in the presence of zirconocene dichloride (zirconium dicyclopentadienyl dichloride). The latter "carboalumination reaction" is believed to cause a syn addition of a methyl group and of the dimethylaluminum group to the triple bond, to provide an intermnediate shown in brackets as Formula 14 in Reaction Scheme 3. The intermediate of Formula 14 is then coupled with a heterocycle derivative of Formula 15 wherein Y, A and B' are defined as above, and X is a I, Br, or $(CH_3)_3Sn$, in the presence of a suitable catalyst, such as tetrakis(triphenylphosphine)palladium $(Pd(PPh_3)_4)$. The latter coupling reaction is usually conducted at room temperature, in an inert gas (preferably argon) atmosphere in an ether type solvent, such as tetrahydrofuran. Formula 16 shows the product of the coupling reaction, which is either a compound within the scope of Formula 2, or a protected derivative or precursor thereof, from which the compounds of the invention can be readily obtained by deblocking reactions, or the like, well known in the art.

An alternative route for obtaining the compounds of

Formula 16 from the intermediate of Formula 14 is to react the latter with iodine in an inert ether type solvent, such as tetrahydrofuran, to obtain the iodovinyl derivative of Formula 17. The compound of Formula 17 is preferably isolated, and coupled with the compound of Formula 15, in the presence of tetrakis(triphenylphosphine)palladium (Pd(PPh$_3$)$_4$) catalyst, or the like, to yield the compound of Formula 16.

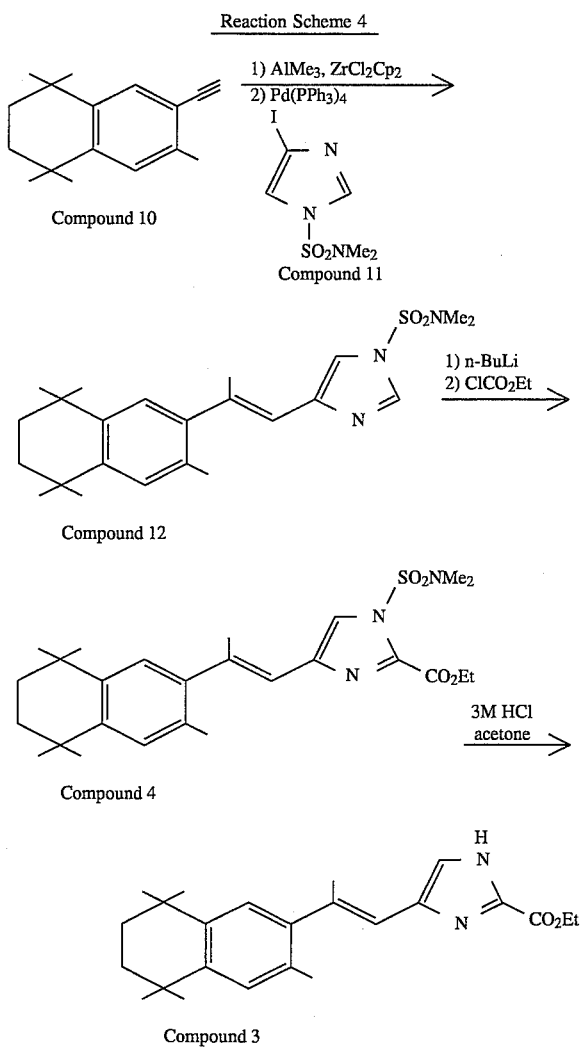

It should be noted in connection with Reaction Schemes 1, 2 and 3 that in all of these reaction schemes heterocycle derivatives corresponding respectively to Formula 7, 11 and 15 can be employed where in the A-B' substituent A is (CH$_2$)$_n$, n is 0, and B' is hydrogen. A carboxylic acid group is then introduced into the molecule, after coupling with the tetrahydronaphthalene moiety, by reaction with strong base (such as n-butyl lithium) and carbon dioxide or ethyl chloroformate. Reaction Scheme 4 illustrates specifically the synthesis of Compound 3 and Compound 4 of the present application. In accordance with this scheme (5,6,7,8-tetrahydro-3,5,5,8,8-pentamethylnaphthalen- 2-yl)acetylene (Compound 10) is reacted with trimethylaluminum in the presence zirconocene dichloride. The resulting "carboaluminated adduct" (not shown in Scheme 4) is reacted in the presence of tetrakis(triphenylphosphine)palladium (Pd(PPh$_3$)$_4$) catalyst, with 1-(N,N-dimethylsulfamoyl)-4-iodoimidazole (Compound 11) which is obtained by iodination from 1-(N, N-dimethylsulfamoyl)imidazole. The latter compound can be obtained in accordance with the chemical literature: Chadwick et al. J. Chem. Soc., Perkin Trans. I 1984, 481–486. The result of the coupling reaction between the carboaluminated adduct derived from Compound 10 and Compound 11 is (E)-4-[2-(5,6,7,8-tetrahydro-3,5,5,8,8-pentamethylnaphthalen- 2-yl)propen-1-yl]-1-(N, N-dimethylsulfamoyl)imidazole (Compound 12). The carboxylic acid ethyl ester moiety is introduced into the molecule by reacting the anion of Compound 12 generated with strong base such as n-butyl lithium, with ethyl chloroformate, to yield ethyl (E)-4-[2-(5,6,7,8-tetrahydro- 3,5,5, 8,8-pentamethylnaphthalen-2-yl)propen-1-yl]-1-(N,N-dimethylsulfamoyl)-2-imidazolecarboxylate (Compound 4). The dimethylsulfamoyl group is removed from the imidazole nitrogen by treatment with acid, to yield ethyl (E)-4-[2-(5,6,7,8-tetrahydro-3,5,5,8,8-pentamethylnaphthalen-2-yl)propen-1-yl]-2-imidazolecarboxylate (Compound 3).

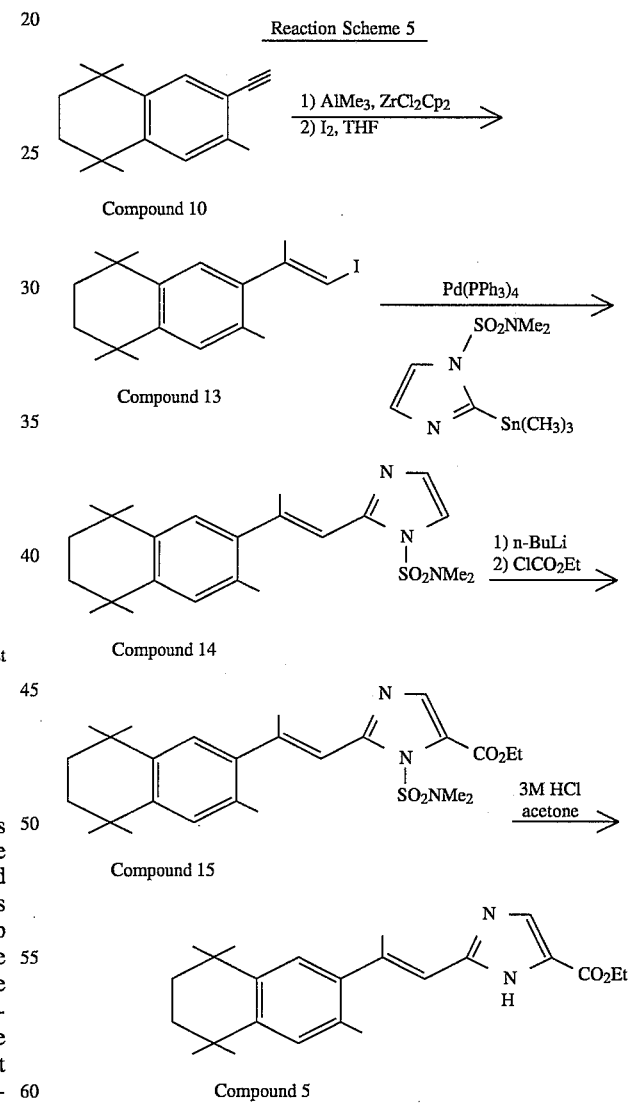

Reaction Scheme 5 illustrates specifically the synthesis of Compound 5 of the present invention. In the course of this synthesis (5,6,7,8-tetrahydro-3,5,5,8,8-pentamethylnaphthalen-2-yl)acetylene (Compound 10) is reacted with trimethylaluminum in the presence zirconocene dichloride and thereafter iodine is added to the "carboaluminated adduct" to yield the "vinyliodide" Compound 13. 2-(Trimethylstannyl)-1-(N,N-dimethylsulfamoyl)imidazole is obtained from 1-(N,N-dimethylsulfamoyl)imidazole by reaction with n-butyl lithium and trimethyltin chloride, and is reacted with Compound 13 in the presence of tetrakis(triphenylphosphine)palladium (Pd(PPh$_3$)$_4$) catalyst to yield (E)-2-[2-(5,6,7,8-tetrahydro- 3,5,5,8,8-pentamethylnaphthalen-2-yl)propen-1-yl]-1-(N,N-dimethylsulfamoyl)imidazole (Compound 14). Compound 14 is converted to the responding 5-carboethoxy derivative (Compound 15) by deprotonation with a strong base, such as n-butyl lithium, and subsequent reaction with ethyl chloroformate. The N,N-dimethylsulfanoyl group is removed from the imidazole nucleus by treatment with acid, to yield Compound 5.

Specific Examples

Methyl (5,6,7,8-tetrahydro-3,5,5,8,8-pentamethylnaphthalen- 2-yl) ketone (Compound 16)

To a suspension of 6.71 g (50.3 mmol) of aluminum chloride in methylene chloride at 0° C. under argon was added a solution of 3.95 g (3.58 mL, 50.3 mmol) of acetyl chloride and 10.21 g (41.9 mmol) of 5,6,7,8-tetrahydro-3,5,5,8,8-pentamethylnaphthalene in methylene chloride. The resulting mixture was allowed to warm to room temperature over a period of 3 hours with stirring. The mixture was recooled to 0° C. and 1N HCl was dropwise added. The mixture was then taken-up in water and extracted three times with methylene chloride. The organic layers were washed with 1N HCl, water, brine, and dried (MgSO$_4$). Solvent was removed in-vacuo and the resulting residue purified using flash chromatography to give the title compound as an ivory solid.

PMR (CDCl$_3$): δ1.28 (6H, s), 1.30 (6H, s), 1.69 (4H, s), 2.49 (3H, s), 2.57 (3H, s), 7.15 (1H, s), 7.67 (1H, s). (±)-1-(5,6,7,8-tetrahydro-3,5,5,8,8-pentamethylnaphthalen-2-yl)ethanol (Compound 17)

To a solution of 4.17 g (17.1 mmol) of methyl (5,6,7,8-tetrahydro-3,5,5,8,8-pentamethylnaphthalen-2yl) ketone (Compound 16) in methanol at 0° C. was portionwise added 0.77 g (20.4 mmol) of sodium borohydride and the resulting suspension stirred at 0° C. for 4 hours. Solvent was removed in-vacuo and the resulting solid taken-up in water, acidified using 1N HCl, and extracted three times with ether. The ether extracts were washed with water, brine and dried (MgSO$_4$). The solvent was removed in-vacuo and resulting residue purified using flash chromatography (SiO$_2$, 10% ethyl acetate in hexanes) to give a single isomer: the title compound as a white solid.

PMR (CDCl$_3$): δ1.28 (12H, m), 1.47 (3H, d, J=6.5 Hz), 1.67 (4H, s), 2.49 (3H, s), 5.08 (1H, m), 7.10 (1H, s), 7.45 (1H, s).
(±) -[1-(5,6,7,8-tetrahydro-3,5,5,8,8-pentamethylnaphthalen- 2-yl)ethan-1-yl]triphenylphosphonium bromide (Compound 18)

To a solution of 3.87 g (15.7 mmol) of (±)-1-( (5,6,7,8-tetrahydro-3,5,5,8,8-pentamethylnaphthalen-2-yl)ethanol (Compound 17) in ether and hexanes at 0° C. under argon, was added 42.4 g (14.9 mL, 157 mmol) of phosphorus tribromide and the resulting mixture stirred for 2 hours. Water was then dropwise added over a period of 30 minutes and the layers separated. The aqueous layer was extracted three times with ether. The ether layers were washed with water, brine, and dried (MgSO$_4$). The solvent was removed in-vacuo and the remaining residue taken-up in benzene. Triphenylphosphine was added and the mixture stirred at room temperature for 24 hours. The mixture was then concentrated in-vacuo and the resulting solid recrystallized from acetonitrile and ethyl acetate and hexanes to give the title compound as a white solid.

PMR (CDCl$_3$): δ0.61 (3H, s), 0.89 (3H, s), 1.27 (6H, s), 1.62 (4H, m), 1.85 (6H, d), 2.04 (3H, dd), 5.19 (2H, m), 6.62 (1H, d), 7.02 (1H, s), 7.43 (6H, m), 7.68 (6H, m), 7.87 (3H, m).
Methyl (3-chloro-5,6,7,8-tetrahydro-5,5,8,8-tetramethylnaphthalen)-2-yl) ketone To a suspension of 13.6 g (102 mmol) of aluminum chloride in 24 mL of methylene chloride at 0° C. under argon was added a solution of 7.98 g (7.23 mL, 102 mmol) of acetyl chloride, 18.88 g (84.8 mmol) of 3-chloro- 5,6,7,8-tetrahydro-3,5,5,8,8-pentamethylnaphthalene in 56 mL of methylene chloride. The resulting mixture was allowed to warm to room temperature over a period of three hours with stirring. The mixture was recooled to 0° C. and 1N HCl was added dropwise. The mixture was then taken-up in water and extracted three times with methylene chloride. The organic layers were washed with 1N HCl, water, brine, and dried (MgSO$_4$). Solvent was removed in-vacuo and the resulting residue distilled (116° C., 3 mm Hg) to give a mixture of starting material and product.

PMR (CDCl$_3$): δ1.27 (12H, s), 1.19 (4H, s), 2.65 (3H, s), 7.31 (1H, s), 7.54 (1H, s). (±)-1-(3-chloro-5,6,7,8-tetrahydro-5,5,8,8-tetramethylnaphthalen- 2-yl)ethanol To a solution of 5.01 g (18.9 mmol) of methyl [3-chloro-5,6,7,8-tetrahydro-5,5,8,8-tetramethylnaphthalen- 2-yl] ketone in methanol at 0° C. was portionwise added 1.0 g (26.4 mmol) of sodium borohydride and the resulting suspension stirred at 0° C. for 2 hours. The mixture was then acidified using 1N HCl, and extracted three times with ether. The ether extracts were washed with water, brine and dried (MgSO$_4$). The solvent was removed in-vacuo and resulting residue purified using flash chromatography (SiO$_2$, 5% ethyl acetate in hexanes) to give the title compound as a white solid.

PMR (CDCl$_3$): δ1.26 (12H, m), 1.48 (3H, d, J=6.5 Hz), 1.67 (4H, s), 1.98 (1H, s), 5.21 (1H, m), 7.23 (1H, s), 7.50 (1H, s).
(±)-[1-(3-chloro-5,6,7,8-tetrahydro-5,5,8,8-tetramethylnaphthalen-2-yl)ethan-1-yl]triphenylphosphonium bromide To a solution of 3.15 g (11.8 mmol) of (±)-1-(3-chloro-5,6,7,8-tetrahydro-5,5,8,8-tetramethylnaphthalen-2-yl) ethanol in ether and hexane stirring at 0° C. under argon, was added dropwise 31.9 g (11.2 mL, 118 mmol) of phosphorus tribromide and the mixture stirred 1.5 hours. Water was then carefully added and the mixture extracted with several portions of ether. The ether extracts were washed with water, sodium bicarbonate, brine, and dried (MgSO$_4$). The solvent was removed in-vacuo and the residual oil taken up in 175 mL of benzene. To this was added 3.09 g (11.8 mmol) of triphenylphosphine and the solution stirred for 24 hours at room temperature. Purification was done using flash chromatography (SiO$_2$, 0.5% ethyl acetate in hexanes, 5% MeOH in methylene chloride) to give the title compound as a white foam.

PMR (CDCl$_3$): δ0.70 (3H, s), 1.02 (3H, s), 1.28 (12H, d, J=15 Hz), 1.62 (4H, m), 2.01 (3H, dd, J=15, 9 Hz), 5.19 (1H, m), 6.79 (1H, s), 7.4–7.9 (16H, m).
3-Bromo-5,6,7,8-tetrahydro-5,5,8,8-tetramethylnaphthalene To a solution of 25 g (137 mmol) of 1,6-dichloro-1,6-dimethylhexane in 28.9 mL (274 mmol) of bromobenzene was portionwise added 11.0 g (82.2 mmol) of aluminum chloride at 0° C. under argon and the resulting suspension stirred for 5 minutes at 0° C. and allowed to warm to room temperature for 15 minutes. 1N HCl was added dropwise.

The mixture was taken-up in water and extracted three times with ether. The ether layers were washed with 1N HCl, sodium bicarbonate, brine, and dried (MgSO$_4$). Purification was done using distillation (110° C., 2 mm Hg) to give the title compound as a yellow solid.

PMR (CDCl$_3$): δ1.25 (6H, s), 1.27 (6H, s), 1.67 (4H, s), 7.16 (1H, d, J=8.5 Hz), 7.23 (1H, dd, J=2.0, 8.5 Hz), 7.40 (1H, d, J=2.1 Hz).

Methyl (3-bromo-5,6,7,8-tetrahydro-5,5,8,8-tetramethylnaphthalen- 2-yl) ketone

To a suspension of 6.16 g (46.3 mmol) of aluminum chloride in methylene chloride at 0° C. under argon was added a solution of 3.29 mL (den=1.104, 46.3 mmol) of acetyl chloride, 10.3 g (38.5 mmol) of 3-bromo-5,6,7,8-tetrahydro- 5,5,8-8-tetramethylnaphthalene in methylene chloride. The resulting mixture was stirred for 2 hours and allowed to warm to room temperature over a period of 16 hours. The mixture was recooled to 0° C. and 1N HCl was added dropwise. The mixture was then taken-up in water and extracted three times with methylene chloride. The organic layers were washed with 1N HCl, water, brine, and dried (MgSO$_4$). Solvent was removed in-vacuo and the resulting residue purified using distillation (116° C., 3 mm Hg) to give a mixture of starting material and product.

PMR (CDCl$_3$): δ1.27 (12H, s), 1.68 (4H, s), 2.64 (3H, s), 7.45 (1H, s), 7.50 (1H, s).

Methyl [3-ethyl-5,6,7,8-tetrahydro-5,5,8,8-tetramethylnaphthalen)- 2-yl] ketone

To a suspension of 4.59 g (34.4 mmol) of aluminum chloride in 20 mL of methylene chloride at −5° C. under argon was added a solution of 2.32 g (2.10 mL, 29.5 mmol) of acetyl chloride and 4.95 g (23 mmol) of 3-ethyl- 5,6,7,8-tetrahydro-5,5,8,8-tetramethylnaphthalene (obtainable in accordance with U.S. Pat. No. 2,897,237, the specification of which is expressly incorporated by reference) in 10 mL of methylene chloride over a period of 1 hour. The resulting mixture was stirred at −10° to +5° C. for 3 hours. The mixture was then taken-up in water and extracted three times with methylene chloride. The organic layers were washed with brine and dried (MgSO$_4$). Solvent was removed in-vacuo and the resulting residue purified using flash chromatography (SiO$_2$, 10% ethyl acetate in hexanes) to give the title compound as a white solid.

PMR (CDCl$_3$): δ1.20 (3H, t, J=7.5 Hz), 1.29 (6H, s), 1.30 (6H, s), 1.69 (4H, s), 2.57 (3H, s), 2.84 (2H, q, J=7.3 Hz), 7.17 (1H, s), 7.59 (1H, s).

Methyl [3-isopropyl-5,6,7,8-tetrahydro-5,5,8,8-tetramethylnaphthalen)-2-yl] ketone To a suspension of 5.80 g (43.5 mmol) of aluminum chloride in 15 mL of methylene chloride at −5° C. under argon was added a solution of 3.20 g (2.90 mL, 41 mmol) of acetyl chloride and 6.58 g (29 mmol) of 3-isopropyl-5,6,7, 8-tetrahydro-5,5,8,8-tetramethylnaphthalene (obtainable in accordance with U.S. Pat. No. 2,879,237, the specification of which is expressly incorporated by reference) in 25 mL of methylene chloride over a period of 1 hour. The resulting mixture was stirred at −5° C. for 2.5 hours. The mixture was then cooled to 0° C., taken-up in water and extracted three times with hexane. The organic layers were washed with brine and dried (MgSO$_4$). Solvent was removed in-vacuo and the resulting residue purified using flash chromatography (SiO$_2$, 5% ethyl acetate in hexanes) to give the title compound as a white solid.

PMR (CDCl$_3$): δ1.22 (6H, s), 1.24 (6H, s), 1.29 (6H, s), 1.69 (4H, s), 2.49 (3H, s), 2.56 (3H, s), 3.50 (1H, pentet, J=6.8 Hz), 7.32 (1H, s), 7.46 (1H, s).

2-Thiazolecarboxaldehyde (Compound 19)

To a solution of 13.1 g (7.20 ml, 79.9 mmol) of 2-bromothiazole in 100 ml of ether at −78° C. under argon, was added dropwise 60 ml of n-butyllithium (96 mmol, 1.6M in hexanes). The resulting mixture was stirred at −78° C. for 45 min and then 8.5 g (9.0 ml, 116 mmol) of dimethylformamide was added. The resulting mixture was stirred 30 min at −78° C., saturated aqueous NaCl and pentane were added and the layers separated. The aqueous layer was brought to pH=8 by adding 3% HCl, and the product extracted into ether and dried (MgSO$_4$). The solution was concentrated and the residual oil purified by column chromatography (SiO$_2$, 30% ether in pentane) to give the product as an orange oil.

PNMR (CDCl$_3$, 300 MHz): d 7.78 (1H, d, J=2.8 Hz), 8.15 (1H, d, J=2.9 Hz), 10.04 (1H, s). (E)-2-[2-(5,6,7,8-tetrahydro-3,5,5,8,8-pentamethylnaphthalen- 2-yl) propen-1-yl] thiazole (Compound 20)

To a suspension of 20.0 g (35 mmol) of (±)-[1-(5,6,7,8-tetrahydro-3,5,5,8,8-pentamethylnaphthalen-2-yl)ethan-1-yl]triphenylphosphonium bromide (Compound 18) in 100 ml of tetrahydrofuran at 0° C. was added 29 ml of n-butyllithium (46 mmol, 1.6M in hexanes). The resulting deep red mixture was stirred at room temperature for 45 min. A solution of 3.87 g (34.2 mmol) of 2-thiazolecarboxaldehyde (Compound 19) in 10 ml of tetrahydrofuran was added and the resulting mixture stirred at room temperature for 17 hours. Brine was added and the products extracted into ether and dried (MgSO$_4$). The solution was concentrated to give a mixture of E- and Z-isomers in a 1:1.5 ratio, respectively. The isomers were separated using column chromatography (SiO$_2$, 10% ethyl acetate in hexanes) to give the E- isomer as a clear oil.

PNMR (CDCl$_3$, 300 MHz): d 1.28 (6H, s), 1.30 (6H, s), 1.68 (4H, s), 2.30 (3H, s), 2.46 (3H, d, J=1 Hz), 6.75 (1H, d, J=1 Hz), 7.12 (2H, s), 7.35 (1H, d, J=3.3 Hz), 7.87 (1H, d, J=3.3 Hz).

(E)-2-[2-(5,6,7,8-tetrahydro-3,5,5,8,8-pentamethylnaphthalen-2-yl)propen-1-yl]-5-thiazolecarboxylic acid (Compound 1)

To a solution of 0.69 g (2.1 mmol) of (E)-2-[2- (5,6,7,8-tetrahydro-3,5,5,8,8-pentamethylnaphthalen-2-yl)propen-1-yl]thiazole (Compound 20) in 25 ml of tetrahydrofuran at −78° C. was added 1.55 ml of n-butyllithium (2.5 mmol, 1.6M in hexanes). The resulting solution was stirred at −78° C. for 30 min. The reaction was purged with carbon dioxide for 72 hours at which time the flask was dry. Brine was added and the products were extracted into ether/ethyl acetate (1:1) and dried (MgSO$_4$). The solution was concentrated and the resulting solid purified by recrystallization (Toluene/acetonitrile=1:10) to give the product.

PNMR (CD$_3$OD, 300 MHz): d 1.27 (6H, s), 1.28 (6H, s), 1.70 (4H, s), 2.26 (3H, s), 2.45 (3H, d, J=1.5 Hz), 6.65 (1H, d, J=1.3 Hz), 7.09 (1H, s), 7.16 (1H, s), 8.34 (1H, s).

(5,6,7,8-tetrahydro-3,5,5,8,8-pentamethylnaphthalen-2yl)acetylene (Compound 10)

n-Butyllithium was added to a solution of freshly distilled diisopropylamine (3.01 mL, 21.5 mmol) and THF (41 mL) at 0° C. under argon. After 10 min, the solution was cooled to −78° C. and a solution of methyl (5,6,7,8-tetrahydro-3,5,5,8,8-pentamethylnaphthalen-2-yl) ketone (Compound 16) and THF was added dropwise. The solution was stirred for 1 h at −78° C. and then diethyl chlorophosphate (3.27 mL, 22.6 mmol) was added. The dry-ice bath was removed, and the solution was allowed to warm to room temperature over 1 hour and added dropwise to a −78° C. solution of lithium diisopropylamide (43.1 mmol) and THF (82 mL) prepared as described above. The resultant mixture was warmed to room temperature over 3 hours and quenched with water. The products were extracted with hexanes, washed with 1N HCl, water, brine, dried (MgSO$_4$) and concentrated under reduced pressure. The residue was purified by flash chromatography (SiO$_2$, hexanes) to give the title compound as a colorless solid (4.3 g, 93%).

PNMR (CDCl$_3$, 300 MHz): d 1.23 (12H, s), 1.64 (s, 4H), 2.38 (s, 3H), 3.20 (s, 1H), 7.10 (s, 1H), 7.41 (s, 1H).

1-N,N-Dimethylsulfamoyl-4-iodoimidazole (Compound 11)

To a solution of 1-N,N-dimethylsulfamoylimidazole (1.0 g, 5.7 mmol) and 50 mL THF at −78° C. was added n-buLi (4.0 mL, 1.6M in hexanes, 6.4 mmol). (The 1-N, N-dimethylsulfamoylimidazole can be obtained in accordance with Chadwick et al. J. Chem. Soc., Perkin Trans. I 1984, 481–486.) After 30 min, a solution of iodine (1.74 g, 6.84 mmol) and THF (10 mL) was added dropwise over 10 min. The solution was stirred for 30 min at −78° C. and the reaction quenched by the addition of 10% aqueous NaHCO$_3$. The organic material was extracted with ethyl ether, washed with 10% aqueous NaS$_2$O$_3$, brine, dried (MgSO$_4$) and concentrated in vacuo. The residue was purified by flash chromatography on silica gel (hexanes/ethyl acetate=3:2) to give the title compound as a light yellow oil (639 mg, 37%) and the corresponding 2-iodoimidazole as a light yellow solid (245 mg, 14%).

PNMR (CDCl$_3$, 300 MHz): d 2.89 (s, 6H) 7.34 (s, 1H), 7.78 (s, 1H).

(E)-4-[2-(5,6,7,8-tetrahydro-3,5,5,8,8-pentamethylnaphthalen-2-yl)propen-1-yl]-1-N, N-dimethylsulfamoylimidazole (Compound 12)

A 2M solution of Me$_3$Al and hexanes (3.33 mL, 6.66 mmol) was added to a solution of zirconocene dichloride (0.974 g, 3.33 mmol) and 8 mL of 1,2-dichloroethane at room temperature under argon. The resulting yellow-green solution was treated with a solution of (5,6,7,8-tetrahydro-3,5,5,8,8-pentamethylnaphthalen-2-yl)acetylene (Compound 10, 0.755 g, 3.33 mmol) and 2 mL of 1,2-dichloroethane and the mixture stirred for 20 hours at room temperature. A solution of 1-N,N-dimethylsulfamoyl-4-iodoimidazole (Compound 11, 0.602 g, 2.0 mmol) and THF (12 mL) was degassed with argon for 10 min and treated with tetrakis(triphenylphosphine)palladium (0.192 g, 0.167 mmol). This solution was then added to the first solution and the reaction stirred at room temperature for 1 hour. 5% aqueous NaHCO$_3$ was added carefully and the organic material was extracted with ethyl ether, washed with brine, dried (MgSO$_4$) and concentrated in vacuo. The residue was purified by flash chromatography on silica gel (hexanes/ethyl acetate=3:1) to give the title compound as a light yellow solid (621 mg, 75%).

PNMR (CDCl$_3$, 300 MHz): d 1.27 (s, 6H) 1.29 (s, 6H), 1.68 (s, 4H), 2.29 (s, 3H), 2.31 (s, 3H), 2.91 (s, 6H), 6.31 (s, 1H), 7.10 (s, 2H), 7.22 (s, 1H), 7.92 (s, 1H).

Ethyl (E)-4-[2-(5,6,7,8-tetrahydro-3,5,5,8,8-pentamethylnaphthalen-2-yl)porpen-1-yl]-1-N,N-dimethylsulfamoyl-2-imidazolecarboxylate (Compound 4)

To a solution of (E)-4-[2-(5,6,7,8-tetrahydro-3,5,5,8,8-pentamethylnaphthalen-2-yl)propen-1-yl]-1-N, N-dimethylsulfamoylimidazole (Compound 12, 0.525 g, 1.26 mmol) and 7.0 mL THF at −78° C. was added n-BuLi (0.944 mL, 1.6M in hexanes, 1.51 mmol). After 30 min, ethyl chloroformate (0.361 mL, 3.78 mmol) was added in one portion. The solution was stirred for 30 min at −78° C. and the reaction quenched by the addition of 10% aqueous NaHCO$_3$. The organic material was extracted with ethyl ether, washed with brine, dried (MgSO$_4$) and concentrated in vacuo. The residue was purified by flash chromatography on silica gel (hexanes/ethyl acetate=9:1) to give the title compound as a light yellow solid (430 mg, 70%).

PNMR (CDCl$_3$, 300 MHz): d 1.26 (s, 6H) 1.29 (s, 6H), 1.46 (t, 3H, J=7.1 Hz), 1.67 (s, 4H), 2.261 (s, 3H), 2.266 (s, 3H), 3.86 (s, 6H), 4.45 (q, 2H, J=7.1 Hz), 6.34 (s, 1H), 7.08 (d, 2H, J=2.5 Hz), 7.48 (s, 1H).

Ethyl (E)-4-[2-(5,6,7,8-tetrahydro-3,5,5,8,8-pentamethylnaphthalen-2-yl)propen-1-yl]-2-imidazolecarboxylate (Compound 3)

Ethyl (E)-4-[2-(5,6,7,8-tetrahydro-3,5,5,8,8-pentamethylnaphthalen-2-yl)propen-1-yl]-1-N, N-dimethylsulfamoyl-2-imidazolecarboxylate (Compound 4, 0.295 g, 0.605 mmol) was dissolved in a solution of 3M HCl (2.5 mL) and acetone (20 mL) at room temperature and the solution stirred for 30 min. The solution was neutralized with 5% aqueous NaHCO$_3$ and the organic material was extracted with dichloromethane, washed with brine, dried (K$_2$CO$_3$) and concentrated in vacuo. The residue was purified by flash chromatography on silica gel (hexanes/ethyl acetate=3:2) to give the title compound as a light yellow solid (430 mg, 70%).

PNMR (acetone-d$^6$, 300 MHz): d 1.259 (s, 6H) 1.264 (s, 6H), 1.33 (t, 3H, J=7.1 Hz), 1.68 (s, 4H), 2.25 (s, 3H), 2.29 (d, 3H, J=1.5 Hz), 4.33 (q, 2H, J=7.1 Hz), 6.32 (s, 1H), 7.11 (2, 1H), 7.15 (s, 1H), 7.38 (s, 1H).

Ethyl (E)-4-[2-(5,6,7,8-tetrahydro-3,5,5,8,8-pentamethylnaphthalen-2-yl)propen-1-yl]-1-methyl-2-imidazolecarboxylate (Compound 2)

Ethyl (E)-4-[2-(5,6,7,8 -tetrahydro-3,5,5,8,8-pentamethylnaphthalen-2-yl)propen-1-yl]-1-N,N-dimethylsulfamoyl-2-imidazolecarboxylate (Compound 4, 70 mg, 0.18 mmol) was dissolved in acetone (10 mL) at room temperature and treated with methyl iodide (0.5 mL) and K$_2$CO$_3$ (350 mg). The suspension was stirred for 30 min, filtered through Celite and concentrated under reduced pressure. The residue was treated with water (5 mL) and the organic material was extracted with ethyl acetate, washed with brine, dried (MgSO$_4$) and concentrated in vacuo. The residue was purified by flash chromatography on silica gel (hexanes/ethyl acetate=5:1) to give the title compound as a light yellow solid (35 mg, 50%).

PNMR (CDCl$_3$, 300 MHz): d 1.56 (s, 6H) 1.29 (s, 6H), 1.44 (t, 3H, J=7.1 Hz), 1.67 (s, 4H), 2.23 (s, 3H), 2.26 (s, 3H), 4.05 (s, 3H), 4.44 (q, 2H, J=7.1 Hz), 6.44 (s, 1H), 7.08 (s, 1H), 7.08 (s, 1H), 7.11 (s, 1H).

(E)-2-(5,6,7,8-tetrahydro-3,5,5,8,8-pentamethylnaphthalen-2-yl)-1-iodopropene (Compound 21)

A 2M solution of Me$_3$Al and hexanes (6.80 mL, 13.6 mmol) was added to a solution of zirconocene dichloride (1.98 g, 6.80 mmol) and 18 mL of 1,2-dichloroethane at room temperature under argon. The resulting yellow-green solution was treated with a solution of (5,6,7,8-tetrahydro-3,5,5,8,8 -pentamethylnaphthalen-2-yl)acetylene (Compound 10, 1.53 g, 6.80 mmol) and 3 mL of 1,2-dichloroethane and the mixture stirred for 19 hours at room temperature. A solution of iodine (2.07 g, 8.13 mmol) and THF (15 mL) was added to the first solution and the reaction stirred at room temperature for 10 min. 5% aqueous Na$_2$S$_2$O$_3$ was added carefully and the organic material was extracted with ethyl ether, washed with brine, dried (MgSO$_4$) and concentrated in vacuo. The residue was purified by flash chromatography on silica gel (hexanes) to give the title compound (1.23 g, 49%) as a mixture that contained 0.59 g of 2-(5,6,7,8-tetrahydro-3,5,5,8,8-pentamethylnaphthalen-2-yl)propene. This biproduct is inert to the next palladium coupling reaction and so the mixture can be used without further purification.

PNMR (CDCl$_3$, 300 MHz): d 1.25 (s, 6H) 1.27 (s, 6H), 1.68 (s, 4H), 2.13 (s, 3H), 2.19 (s, 3H), 6.97 (s, 1H), 7.23 (s, 1H).

(E)-2-[2-(5,6,7,8-tetrahydro-3,5,5,8,8-pentamethylnaphthalen-2-yl)propen-1-yl]-1-N, N-dimethylsulfamoylimidazole (Compound 22)

To a solution of 1-N,N-dimethylsulfamoylimidazole (0.64 g, 3.67 mmol) and 10 mL THF at −78° C. was added n-BuLi (2.3 mL, 1.6M in hexanes, 3.67 mmol). After 30 min, a solution of trimethyltin chloride (3.7 mL, 1.0M in THF, 3.67 mmol) was added dropwise over 10 min and the solution stirred for 30 min at −78° C. (E)-2-(5,6,7,8-tetrahydro-3,5,5,8,8-pentamethylnaphthalen-2-yl)-1-iodopropene (Compound 21, 1.23 g, 3.34 mmol) and tetrakis(triphenylphosphine)palladium (0.20 g, 0.172 mmol) were added to the solution and the reaction stirred at room temperature overnight. 5% aqueous NaHCO$_3$ was added and the organic material was extracted with ethyl ether, washed with brine, dried (MgSO$_4$) and concentrated in vacuo. The residue was purified by flash chromatography on silica gel (hexanes/ethyl acetate=4:1) to give the title compound as a light yellow solid (770 mg, 55%).

PNMR (CDCl$_3$, 300 MHz): d 1.26 (s, 6H) 1.29 (s, 6H), 1.68 (s, 4H), 2.28 (s, 3H), 2.46 (s, 3H), 2.87 (s, 6H), 6.65 (s, 1H), 7.08 (s, 2H), 7.14 (d, 1H, J=1.7 Hz), 7.31 (d, 1H, J=1.7 Hz).

Ethyl (E)-2-[2-(5,6,7,8-tetrahydro-3,5,5,8,8-pentamethylnaphthalen-2-yl)propen-1-yl]-1-N, N-dimethylsulfamoyl-5-imidazolecarboxylate (Compound 8)

To a solution of (E)-2-[2-(5,6,7,8-tetrahydro-3,5,5,8,8-pentamethylnaphthalen-2-yl)propen-1-yl]-1-N, N-dimethylsulfamoylimidazole (Compound 22, 0.47 g, 1.13 mmol) and 8.0 mL THF at −78° C. was added n-BuLi (0.78 mL, 1.6M in hexanes, 1.24 mmol). After 30 min, ethyl chloroformate (0.325 mL, 3.39 mmol) was added quickly. The solution was stirred for 30 min at −78° C. and the reaction quenched by the addition of 10% aqueous NaHCO$_3$. The organic material was extracted with ethyl ether, washed with brine, dried (MgSO$_4$) and concentrated in vacuo. The residue was purified by flash chromatography on silica gel (hexanes/ethyl acetate=9:1) to give the title compound as a viscous yellow oil (343 mg, 70%).

PNMR (CDCl$_3$, 300 MHz): d 1.26 (s, 6H) 1.29 (s, 6H), 1.38 (t, 3H, J=7.1 Hz), 1.67 (s, 4H), 2.23 (s, 3H), 2.24 (d, 3H, J=1.5 Hz), 3.03 (s, 6H), 4.34 (g, 2H, J=7.1 Hz), 6.56 (d, 1H, J=1.5 Hz), 7.10 (s, 1H), 7.11 (s, 1H), 7.58 (s, 1H).

(E)-2-[2-(5,6,7,8-tetrahydro-3,5,5,8,8-pentamethylnaphthalen-2-yl)propen-1-yl]-1-N, N-dimethylsulfamoyl-5-imidazolecarboxylic acid (Compound 9)

Ethyl (E)-2-[2-(5,6,7,8-tetrahydro-3,5,5,8,8-pentamethylnaphthalen-2-yl)propen-1-yl]-1-N, N-dimethylsulfamoyl-5-imidazolecarboxylate (Compound 8, 0.09 g, 0.19 mmol) was dissolved in ethanol (4 mL) and treated with 1N aqueous KOH (1 mL). The solution was stirred for 20 hours at 50° C. and concentrated under vacuum. The residue was treated with ether (10 mL) and water (1 mL) and neutralized with saturated aqueous NH$_4$Cl. The layers were separated and the aqueous layer extracted with ether. The organic extracts were combined, washed with brine, dried (MgSO$_4$), filtered and concentrated under reduced pressure. The residue was purified by flash chromatography (SiO$_2$, methanol:dichloromethane=1:9) to give the title compound as a pale yellow powder (60 mg, 71%).

PNMR (CD$_3$OD, 300 MHz): d 1.34 (s, 6H) 1.35 (s, 6H), 1.77 (s, 4H), 2.35 (d, 3H, J=1.3 Hz), 2.36 (s, 3H), 3.09 (s, 6H), 6.53 (d, 1H, J=1.3 Hz), 7.18 (s, 1H), 7.21 (s, 1H), 7.58 (s, 1H).

Ethyl (E)-2-[2-(5,6,7,8-tetrahydro-3,5,5,8,8-pentamethylnaphthalen-2-yl)propen-1-yl]-5-imidazolecarboxylate (Compound 5)

Ethyl (E)-2-[2-(5,6,7,8-tetrahydro-3,5,5,8,8-pentamethylnaphthalen-2-yl)propen-1-yl]-1-N,N-dimethylsulfamoyl-5-imidazolecarboxylate (Compound 8, 0.25 g, 0.51 mmol) was dissolved in a solution of 3M HCl (1 mL) and acetone (5 mL) at room temperature and the solution stirred for 30 min. The solution was neutralized with 5 % aqueous NaHCO$_3$ and the organic material was extracted with dichloromethane, washed with brine, dried (K$_2$CO$_3$) and concentrated in vacuo. The residue was purified by flash chromatography on silica gel (hexanes/ethyl acetate=2:1) to give the title compound as an inseparable 3:1 mixture of tautomers which were used without further purification (178 mg, 91%).

PNMR (CDCl$_3$, 300 MHz): major tautomer: d 1.23 (s, 6H) 1.26 (s, 6H), 1.37 (t, 3H, J=7.1 Hz), 1.68 (s, 4H), 2.26 (s, 3H), 2.53 (s, 3H), 4.35 (q, 2H, J=7.1 Hz), 6.20 (s, 1H), 7.08 (s, 1H), 7.11 (s, 1H), 7.78 (s, 1H). minor tautomer: d 1.21 (s, 6H) 1.24 (s, 6H), 1.39 (t, 3H, J=7.1 Hz), 1.67 (s, 4H), 2.26 (s, 3H), 2.49 (s, 3H), 4.40 (q, 2H, J=7.1 Hz), 6.23 (s, 1H), 7.07 (s, 1H), 7.10 (s, 1H), 7.76 (s, 1H).

(E)-2-[2-(5,6,7,8-tetrahydro-3,5,5,8,8-pentamethylnaphthalen-2-yl)propen-1-yl]-5-imidazolecarboxylic acid (Compound 6)

Ethyl (E)-2-[2-(5,6,7,8-tetrahydro-3,5,5,8,8-pentamethylnaphthalen-2-yl)propen-1-yl]-5imidazolecarboxylate (Compound 5, 0.043 g, 0.153 mmol) was dissolved in ethanol (2 mL) and treated with 2N aqueous KOH (0.5 mL). The solution was stirred for 20 hours at 50° C. and concentrated under vacuum. The residue was treated with ether (10 mL) and water (1 mL) and neutralized with saturated aqueous NH$_4$Cl. The layers were separated and the aqueous layer extracted with ethyl acetate. The organic extracts were combined, washed with brine, dried (MgSO$_4$), filtered and concentrated under reduced pressure. The residue was passed through a small plug of silica gel (methanol) to give the title compound as a pale yellow powder (40 mg, 80%).

PNMR (CD$_3$OD, 300 MHz): d 1.26 (s, 6H) 1.27 (s, 6H), 1.69 (s, 4H), 2.27 (d, 3H, J=1.3 Hz), 2.37 (s, 3H), 3.09 (s, 6H), 6.17 (s, 1H), 7.08 (s, 1H), 7.13 (s, 1H), 7.69 (s, 1H).

Ethyl (E)-2-[2-(5,6,7,8-tetrahydro-3,5,5,8,8-pentamethylnaphthalen-2-yl)propen-1-yl]-1-methyl-5-imidazolecarboxylate (Compound 7)

Ethyl (E)-2-[2-(5,6,7,8-tetrahydro-3,5,5,8,8-pentamethylnaphthalen-2-yl)propen-1-yl]-5-imidazolecarboxylate (Compound 5, 25 mg, 0.066 mmol) was dissolved in acetone (3 mL) at room temperature and treated with methyl iodide (0.025 mL) and K$_2$CO$_3$ (100 mg). The suspension was stirred for 24 hours, filtered through Celite and concentrated under reduced pressure. The residue was treated with water (5 mL) and the organic material was extracted with ethyl acetate, washed with brine, dried (MgSO$_4$) and concentrated in vacuo. The residue was purified by flash chromatography on silica gel (hexanes/ethyl acetate=5:1) to give the title compound as a light yellow solid (14 mg, 54%).

PNMR (CDCl$_3$, 300 MHz): d 1.27 (s, 6H) 1.30 (s, 6H), 1.39 (t, 3H, J=7.1 Hz), 1.68 (s, 4H), 2.30 (s, 3H), 2.47 (d, 3H, J=1.4 Hz), 3.63 (s, 3H), 4.37 (q, 2H, J=7.1 Hz), 6.10 (d, 1H, J=1.4 Hz), 7.09 (s, 1H), 7.12 (s, 1H), 7.56 (s, 1H).

What is claimed is:

1. A compound of the formula

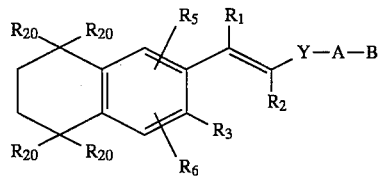

where $R_1$ is lower alkyl, Cl, Br, or I;

$R_2$ is H, lower alkyl, Cl, Br, or I;

$R_3$ is lower alkyl, Cl, Br, I, $OR_{11}$, $SR_{11}$, $OCOR_{11}$, $SCOR_{11}$, $NH_2$, $NHR_{11}$, $N(R_{11})_2$, $NHCOR_{11}$, or $NR_{11}$—$COR_{11}$;

$R_5$ and $R_6$ independently are H, lower alkyl, Cl, Br, I, lower alkoxy or lower thioalkoxy of 1 to 6 carbons;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is COOH or a pharmaceutically acceptable salt thereof, $COOR_8$, $CONR_9R_{10}$, —$CH_2OH$, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, $R_{11}$ is alkyl of 1 to 10 carbons, phenyl or lower alkylphenyl, $R_{12}$ is lower alkyl, and $R_{13}$ is divalent alkyl radical of 2–5 carbons;

$R_{20}$ is independently H or lower alkyl, and

Y is oxazole, thiazole, imidazole, isothiazole or isoimidazole which may be optionally substituted on a carbon or on a nitrogen with an $R_{21}$ group which is lower alkyl, or $SO_2NR_{22}R_{23}$ where $R_{22}$ is lower alkyl and $R_{23}$ is hydrogen or lower alkyl.

2. A compound of claim 1 wherein A is $(CH_2)_n$ and n is 0.

3. A compound of claim 1 wherein B is COOH or a pharmaceutically acceptable salt thereof, $COOR_8$, or $CONR_9R_{10}$.

4. A compound of claim 1 wherein $R_3$ is methyl.

5. A compound of claim 1 wherein $R_1$ is methyl.

6. A compound of claim 1 wherein $R_2$ is hydrogen.

7. A compound of claim 1 wherein $R_{20}$ is methyl.

8. A compound of claim 1 wherein $R_5$ and $R_6$ are hydrogen.

9. A compound of claim 1 wherein Y is thiazole.

10. A compound of claim 1 wherein Y is imidazole.

11. A compound of claim 1 wherein Y is imidazole substituted on a nitrogen with the $R_{21}$ group.

12. A compound of claim 1 wherein Y is oxazole.

13. A compound of the formula

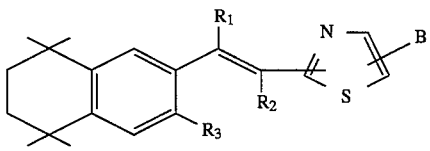

where $R_1$ is lower alkyl;

$R_2$ is H or lower alkyl;

$R_3$ is lower alkyl, Cl, Br, or I, and

B is COOH or a pharmaceutically acceptable salt thereof, $COOR_8$, or $CONR_9R_{10}$, where $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl.

14. A compound of claim 13 where the thiazole ring is 2,5-substituted with the group B occupying the 5 position.

15. A compound of claim 14 where $R_2$ is H, and $R_1$ and $R_3$ are methyl.

16. A compound of claim 15 where B is COOH or a pharmaceutically acceptable salt thereof, or $COOC_2H_5$.

17. A compound of the formula

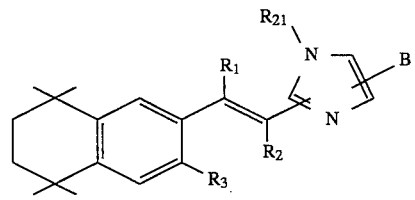

where $R_1$ is lower alkyl;

$R_2$ is H or lower alkyl;

$R_3$ is lower alkyl, Cl, Br, or I, and

B is COOH or a pharmaceutically acceptable salt thereof, $COOR_8$, or $CONR_9R_{10}$, where $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5 to 10 carbons, or phenyl or lower alkylphenyl, and $R_{21}$ is H, or lower alkyl, or $SO_2NR_{22}R_{23}$ where $R_{22}$ is lower alkyl and $R_{23}$ is hydrogen or lower alkyl.

18. A compound of claim 17 where $R_2$ is H, and $R_1$ and $R_3$ are methyl.

19. A compound of claim 18 where the imidazole ring is 2,4 substituted with the B group occupying the 2-position.

20. A compound of claim 19 where $R_{21}$ is $CH_3$.

21. A compound of claim 20 where B is COOH or a pharmaceutically acceptable salt thereof, or $COOC_2H_5$.

22. A compound of claim 19 where $R_{21}$ is H.

23. A compound of claim 22 where B is COOH or a pharmaceutically acceptable salt thereof, or $COOC_2H_5$.

24. A compound of claim 19 where $R_{21}$ is $SO_2N(CH_3)_2$.

25. A compound of claim 24 where B is COOH or a pharmaceutically acceptable salt thereof, or $COOC_2H_5$.

26. A compound of claim 18 where the imidazole ring is 2,5 substituted with the B group occupying the 5-position.

27. A compound of claim 26 where $R_{21}$ is $CH_3$.

28. A compound of claim 27 where B is COOH or a pharmaceutically acceptable salt thereof, or $COOC_2H_5$.

29. A compound of claim 26 where $R_{21}$ is H.

30. A compound of claim 29 where B is COOH or a pharmaceutically acceptable salt thereof, or $COOC_2H_5$.

31. A compound of claim 26 where $R_{21}$ is $SO_2N(CH_3)_2$.

32. A compound of claim 31 where B is COOH or a pharmaceutically acceptable salt thereof, or $COOC_2H_5$.

* * * * *

UNITED STATES PATENT AND TRADEMARK OFFICE
CERTIFICATE OF CORRECTION

PATENT NO. : 5,475,113  
DATED : December 12, 1995  
INVENTOR(S) : Chandraratna

Page 1 of 2

It is certified that error appears in the above-indentified patent and that said Letters Patent is hereby corrected as shown below:

Column 11, line 42, "A-B B" should be --A-B--;

Column 13, line 21, "8tetrahydronaph-" should be --8-tetrahydronaph- --;

Column 18, line 48, "(($Ch_3)_3Al$)" should be --(($CH_3)_3Al$)--;

Column 18, line 56, "($Ch_3)_3Sn$" should be --($CH_3)_3Sn$--;

Column 21, line 56, "((5,6,7,8-" should be --(5,6,7,8- --;

Column 28, line 29, "-5imidazolecarboxylate" should be

--5-imidazolecarboxylate--.

UNITED STATES PATENT AND TRADEMARK OFFICE
CERTIFICATE OF CORRECTION

PATENT NO. : 5,475,113
DATED : December 12, 1995
INVENTOR(S) : Chandraratna

It is certified that error appears in the above-indentified patent and that said Letters Patent is hereby corrected as shown below:

Column 2, line 29, "substitited" should be --substituted--;

Column 20, line 4, please delete "between";

Column 25, line 10, "n-buLi" should be --n-BuLi--.

Signed and Sealed this

Twenty-fifth Day of February, 1997

Attest:

BRUCE LEHMAN

*Attesting Officer*   *Commissioner of Patents and Trademarks*